United States Patent
Aso et al.

(10) Patent No.: US 7,303,823 B2
(45) Date of Patent: Dec. 4, 2007

(54) METHOD OF FORMING ANTIBACTERIAL LAYER CONTAINING METAL-MODIFIED APATITE

(75) Inventors: Noriyasu Aso, Kawasaki (JP); Masato Wakamura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 469 days.

(21) Appl. No.: 10/878,020

(22) Filed: Jun. 29, 2004

(65) Prior Publication Data

US 2004/0241431 A1 Dec. 2, 2004

Related U.S. Application Data

(62) Division of application No. 10/351,301, filed on Jan. 27, 2003, now Pat. No. 6,777,357.

(30) Foreign Application Priority Data

May 21, 2002 (JP) ............................ 2002-146110

(51) Int. Cl.
*B32B 9/00* (2006.01)
*B32B 19/00* (2006.01)

(52) U.S. Cl. .................... 428/689; 428/701; 428/702; 428/432

(58) Field of Classification Search .................... None
See application file for complete search history.

(56) References Cited

U.S. PATENT DOCUMENTS

| | | | |
|---|---|---|---|
| 5,304,577 A | 4/1994 | Nagata et al. | 524/417 |
| 5,609,633 A | 3/1997 | Kokubo | 424/423 |
| 5,877,387 A | 3/1999 | Park et al. | 518/703 |
| 6,001,394 A | 12/1999 | Daculsi et al. | 424/489 |
| 6,585,946 B1 | 7/2003 | Bonfield et al. | 423/308 |
| 2002/0127260 A1 | 9/2002 | Riman et al. | 424/423 |

FOREIGN PATENT DOCUMENTS

| | | |
|---|---|---|
| DE | 3301122 A | 7/1984 |
| EP | 511868 A2 | 11/1992 |
| JP | 59060348 A | 4/1984 |
| JP | 11172747 | 6/1999 |
| JP | 11-195345 | 7/1999 |
| JP | 2000-327315 | 11/2000 |

*Primary Examiner*—Jennifer C. McNeil
*Assistant Examiner*—Jonathan Langman
(74) *Attorney, Agent, or Firm*—Kratz, Quintos & Hanson, LLP

(57) ABSTRACT

A method is provided for forming an antibacterial layer containing a metal-modified apatite. First, an apatite-containing liquid is prepared, which contains both an inorganic coating agent and 0.01~5 wt % of metal-modified apatite powder. Then, the apatite-containing liquid is applied to an object. The applied liquid is dried and hardened to form the desired antibacterial layer.

4 Claims, 4 Drawing Sheets

METHOD OF FORMING ANTIBACTERIAL LAYER CONTAINING METAL-MODIFIED APATITE

This is a Divisional Application of U.S. patent application Ser. No. 10/351,301, filed on Jan. 27, 2003, now U.S. Pat. No. 6,777,357 which is hereby incorporated by reference.

BACKGROUND OF THE INVENTION

1. Field of the Invention

The present invention relates to a method of forming an antifouling or antibacterial layer containing metal-modified apatite. The present invention also relates to an electronic device partially or entirely coated with such a layer.

2. Description of the Related Art

Portable electronic devices, in particular cellular phones, may always be carried by the users and frequently touched for operation, in comparison with much heavier household appliances such as washing machines or refrigerators. Eventually, particular parts of the portable devices will become dirty by the sebum of the user's hands and further by the dust accumulated on the sebum. If the user is a smoker, the device may also be contaminated by the tar of cigarettes. Unfavorably, these accumulated dust or cigarette tar often gives rise to the proliferation of bacteria at the contaminated portion of the device.

In light of the above, recent portable electronic devices are often subjected to antibacterial treatment before they are put on the market. The desired antibacterial function can be provided by using a photocatalytic semiconductor in producing an outward coating of the device.

In a photocatalytic semiconductor, an electron can make a transition from the valence band to the conduction band when the semiconductor absorbs radiation having an energy corresponding to the band gap between the valence band and the conductor band. Due to the transition, a positively charged hole occurs in the valence band. When a pollutant comes into contact with the semiconductor, the electron present in the conduction band will move onto the pollutant, thereby reducing the pollutant. Then, the hole in the valence band strips the electron from the pollutant, to oxidize the pollutant.

When $TiO_2$ is used as a photocatalytic substance, the transit electron in the conduction band reduces the oxygen in the air, thereby producing a super-oxydo-anion ($O_2^-$). On the other hand, the hole occurring in the valence band oxidizes water present on the surface of the $TiO_2$, thereby producing a hydroxy radical (OH), which is a very strong oxidative molecule. Thus, while an organic compound is held in contact with the $TiO_2$, it will be decomposed to water and carbon dioxide. Such an organics-degrading material as $TiO_2$ is widely used for antibacterial or antifouling purposes.

Japanese patent application laid-open No. 11(1999)-195345, for example, discloses an antibacterial technique in which photocatalytic $TiO_2$ is applied to the push buttons of an electronic device. Unfavorably, $TiO_2$ has a weak adsorbing power with the contaminants. Thus, to put the antibacterial or antifouling function of the $TiO_2$ to effective use, the contaminants need to be held in proper contact with the $TiO_2$.

Japanese patent application laid-open No. 2000-327315 discloses a contact-improving technique between contaminants and $TiO_2$. Specifically, the JP document teaches that $TiO_2$ is combined, on the scale of atoms, with highly adsorptive calcium hydroxy apatite (CaHAP, or $Ca_{10}(PO_4)_6(OH)_2$), to provide metal-modified apatite. The metal-modified apatite has such a structure as obtained by partially replacing Ca contained in the crystalline calcium hydroxyapatite with Ti. The site of the introduced Ti locally provides a chemical structure resembling that of photocatalytic titanium dioxide. The combination of the "quasi-titanium dioxide" structure and the CaHAP is advantageous in that objectionable organics can be held in appropriate contact with the photocatalytic site by the adsorptive CaHAP.

Generally, a greater amount of metal-modified apatite needs to be used for more effective antibacterial or antifouling function. However, according to the method of JP No. 2000-327315, the metal-modified apatite is obtained as white powder. Thus, when the metal-modified apatite is used in an amount sufficient enough to take effect for antibacterial purposes, the resultant appearance of the electronic device may not be attractive due to the inevitable whiteness of the metal-modified apatite. Another problem of the conventional metal-modified apatite is that the particles of the metal-modified apatite powder tend to cohere and form a number of lumps in a solvent. Application of such a lumpy antibacterial material may lead to an unacceptably bad texture of the product.

SUMMARY OF THE INVENTION

The present invention has been proposed under the circumstances described above. It is, therefore, an object of the present invention to provide a method of forming an antibacterial or antifouling layer which contains metal-modified apatite but still has a great transparency. Another object of the present invention is to provide a coating agent used for the method. The present invention also provides an electronic device having its part or parts covered by a metal-modified apatite containing layer.

According to a first aspect of the present invention, there is provided a method of forming a layer containing metal-modified apatite. In accordance with the method, an apatite-containing liquid is prepared, which contains both an inorganic coating agent and 0.01~5 wt % of metal-modified apatite powder. Then, the apatite-containing liquid is applied to an object.

The "metal-modified apatite" mentioned above may be obtained by partially replacing a metallic element in the crystalline structure of a material apatite with a "photocatalytic metal element." A metal element is referred to as "photocatalytic" when it can serve as the photocatalytic center in an oxide. Preferably, the inorganic coating agent may be highly transparent, having a transmission rate of no smaller than 90% for visible light.

The material apatite used to produce the metal-modified apatite of the present invention can be generally expressed by the empirical formula: $A_x(BO_y)_zX_s$. In certain applications, the symbol A may be replaced by metallic elements such as Ca, Co, Ni, Cu, Al, La, Cr and Mg, the symbol B by P or S, and the symbol X by a hydroxyl group (—OH) or halogen (F, Cl, etc.). Examples of the material apatite may be metallic salts of hydroxyapatite, fluorapatite and chlorapatite, and others may be tricalcium orthophosphate, dibasic calcium phosphate, etc. According to the present invention, preferably the material apatite may be hydroxyapatite, in particular calcium hydroxyapatite (CaHAP, or $Ca_{10}(PO_4)_6(OH)_2$).

CaHAP is highly adsorptive especially with respect to organics such as proteins. Also, CaHAP strongly adsorbs mold and bacteria, thereby preventing them from proliferating.

Examples of photocatalytic metal elements are titanium (Ti), zinc (Zn), tungsten (W), manganese (Mn), tin (Sn), indium (In) and iron (Fe). When one of these elements is integrated into the crystalline structure of the material apatite, a "photocatalytic sub-structure" is produced in the apatite crystal. More specifically, referring to the above-noted empirical formula $[A_x(BO_y)_zX_s]$, the photocatalytic sub-structure is provided by the combination of a photocatalytic metal element replacing the symbol A and the oxygen O in the formula.

In accordance with the method of the present invention, the resultant antibacterial layer contains a small amount of metal-modified apatite (0.01~5 wt %), which is advantageous to making the layer highly transparent. At the same time, it has been found that the layer of the present invention can function as a very effective antibacterial coating, in spite of the small amount of metal-modified apatite material.

Preferably, the preparation of the apatite-containing liquid may include a preliminary process in which a powder of metal-modified apatite is dispersed in an alcohol solvent. The preparation may also include a mixing process in which the alcohol solvent with the metal-modified apatite dispersed is added to an inorganic coating material.

Preferably, the metal-modified apatite dispersed in the alcohol solvent may be composed of a plurality of particles which are movable relative to each other, each of the particles having a diameter of no greater than 5 μm.

Preferably, the particles having the diameter of no greater than 5 μm may be obtained by ball milling or filtering of material metal-modified apatite.

Preferably, the metal-modified apatite may be obtained by partially replacing Ca of calcium hydroxyapatite by Ti. The Ti—CaHAP has both an excellent adsorbing power stemming from the CaHAP and an excellent photocatalytic power stemming from the titanium oxide.

Preferably, the inorganic coating agent may comprise heatless glass, which can form an inorganic glass coating at room temperature. The heatless glass may contain 70~80 wt % of an alcohol-solvable inorganic resin, 5~12 wt % of isopropyl alcohol, 3~4 wt % of methanol, and 2~3 wt % of dibutyl tin diacetate.

According to a second aspect of the present invention, there is provided a coating agent comprising an inorganic coating material and 0.01~5 wt % of metal-modified apatite powder.

According to a third aspect of the present invention, there is provided an electronic device comprising: a target portion of antibacterial treatment; and a layer covering the target portion. The layer contains an inorganic coating agent and 0.01~5 wt % of metal-modified apatite powder.

Preferably, the metal-modified apatite may be obtained by partially replacing Ca of calcium hydroxyapatite by Ti.

Preferably, the ratio of Ti to a total sum of Ca and Ti in the metal-modified apatite may be 3~11 mol %.

Preferably, the metal-modified apatite may comprise secondary particles each having a diameter of no greater than 5 μm.

Other features and advantages of the present invention will become apparent from the detailed description given below with reference to the accompanying drawings.

DETAILED DESCRIPTION OF THE PREFERRED EMBODIMENT

Preferred embodiments of the present invention will be described below with reference to the accompanying drawings.

Figure 1:
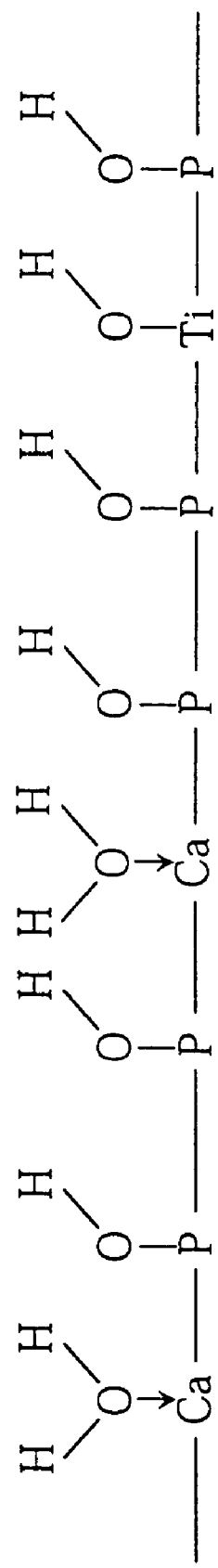
FIG. 1 schematically shows the chemical structure of the metal-modified apatite used for the method of the present invention.

A metal-modified apatite of the present invention is provided by a combination of a photocatalytic metal oxide and a base apatite. Examples of metals used for effecting the desired photocatalysis are titanium (Ti), zinc (Zn), tungsten (W), manganese (Mn), tin (Sn), indium (In) and iron (Fe). The base apatite may be metallic salts of hydroxyapatite, fluorapatite and chlorapatite. FIG. 1 schematically shows the chemical structure of a superficial part of Ti—CaHAP.

As seen from FIG. 1, the integration of Ti produces a photocatalytic substructure in the crystalline CaHAP, with the Ti being the active center. In the Ti—CaHAP, the photocatalytic portions ("catalyst sites") and the "adsorptive sites" are both distributed in the surface of the crystalline substance. Due to this, the Ti—CaHAP is not only highly adsorptive but also highly photocatalytic.

The function of the Ti—CaHAP is as follows. Upon irradiation of light, the quasi-$SiO_2$ catalyst site of the Ti—CaHAP produces a hydroxy radical (OH) from the adsorbed water. The adsorptive site, on the other hand, adsorbs organics. The adsorbed organics are moved by surface diffusion over the Ti—CaHAP surface toward the catalyst site. Then, as coming close enough to the catalyst site, the organics are degraded due to the oxidation by the hydroxy radical. Further, without such a catalytic function, it is possible to prevent the proliferation of bacteria by adsorbing the bacteria strongly at the adsorptive site in the Ti—CaHAP. This means that the Ti—CaHAP can work as an antibacterial substance even when it is not irradiated by light (and hence the catalyst site is not exerting the photocatalysis).

With the use of the above Ti—CaHAP, an antibacterial coating that is effective both in light and dark places can be formed on an electronic device.

The ratio of the photocatalytic metal to all the metal components contained in the crystalline structure of the metal-modified apatite may be 3~11 mol % for proper manifestation of both the adsorptive and photocatalytic functions of the apatite. Taking the Ti—CaHAP for example, the ratio Ti/(Ti+Ca) should be in a range of 0.03-0.11 (in mole fraction). If the ratio is greater than 11 mol %, the crystalline structure may be unduly dislocated. If the ratio is smaller than 3 mol %, the resultant catalytic sites are less in number, which may allow the adsorbed organics to remain undegraded.

Figure 2:
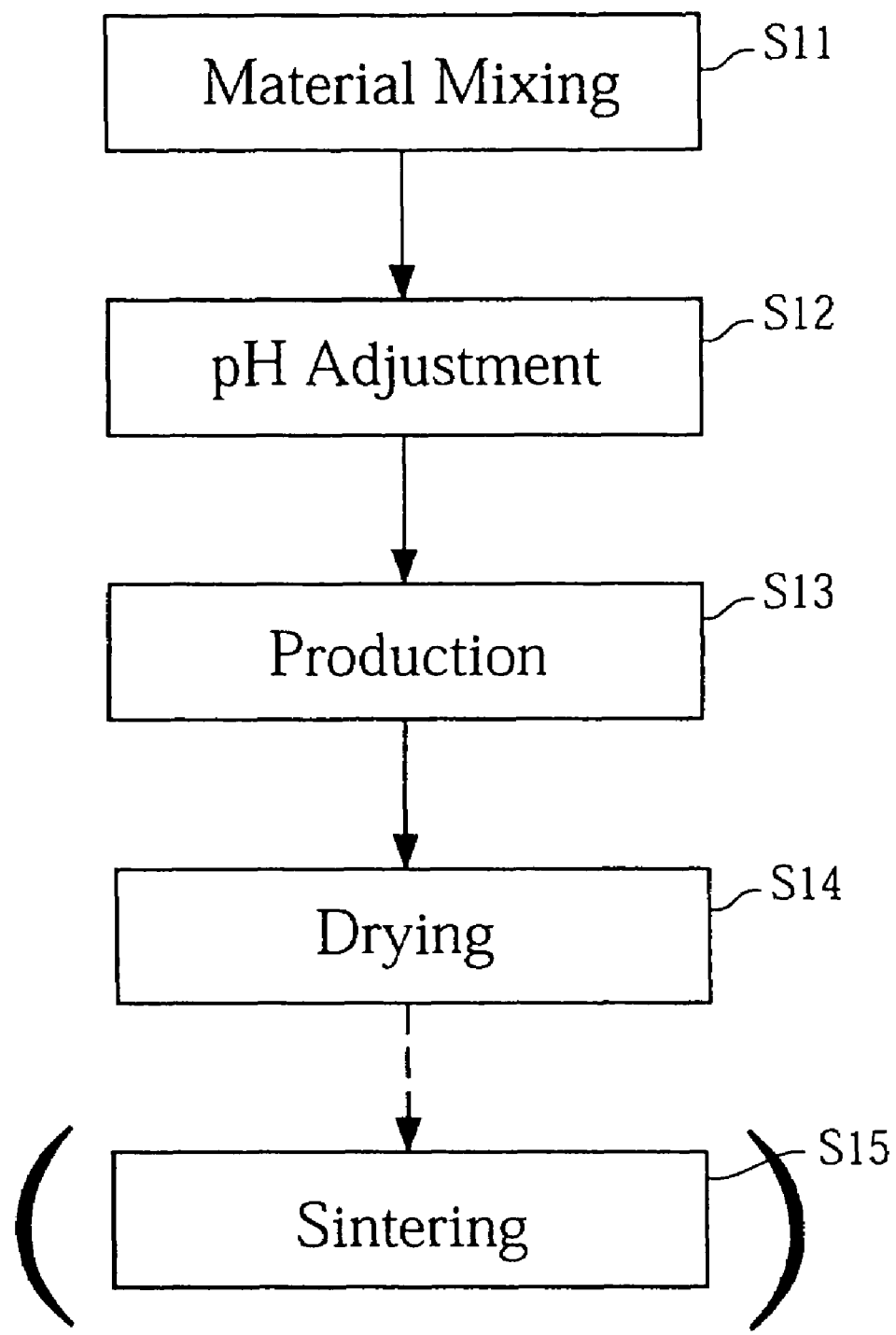
FIG. 2 shows how the metal-modified apatite of the present invention is produced.

Referring now to FIG. 2, the flow chart shows a fabrication procedure of the metal-modified apatite in accordance with the present invention. First, at Step 11 (S11), materials required for producing the desired metal-modified apatite are mixed. Supposing that the material apatite is represented by $A_x(BO_y)_zX_s$, the prescribed amounts of A, $BO_y$, X and photocatalytic metal ion are put into an aqueous solution and stirred. When Ti—CaHAP is expected to be produced, use may be made of calcium nitrate as the supply source of calcium. As the source of $PO_4$, phosphoric acid may be used. The hydroxyl group may be supplied from an alkaline solution to be used for the subsequent pH adjustment step (to be described below), where the alkaline solution may be ammonia water, potassium hydroxide water, or sodium hydroxide water. The supply source of the photocatalytic metal Ti may be titanium chloride or titanous sulfate.

Then, at Step 12, the material solution prepared in the above manner is subjected to pH adjustment so that the production of the desired metal-modified apatite is begun. In performing the pH adjustment use may be made of ammonia water, potassium hydroxide water, or sodium hydroxide water. To produce Ti—CaHAP, the pH of the material solution may be adjusted to range 8 to 10.

Then, at Step 13, the generation of the metal-modified apatite is promoted so as to improve the crystallinity of the resultant compounds. Specifically, apatite components and photocatalytic metal are partially precipitate (coprecipitation). To this end, the above-mentioned material solution is subjected to aging at 100° C. for six hours. As a result, highly crystalline metal-modified apatite is obtained. In an instance of Ti—CaHAP, Ti ion is integrated into the apatite crystalline structure at the location of Ca during the coprecipitation, whereby the growth of the Ti—CaHAP is promoted.

Then, at Step 14, the metal-modified apatite obtained at Step 13 is dried. Specifically, the metal-modified apatite precipitated by Step 13 is filtered out, washed by pure water and then dried at temperatures ranging from 100 to 200° C. By this step, the liquid component stemming from the material solution is removed from the metal-modified apatite.

If necessary, the obtained metal-modified apatite powder is subjected to sintering at Step 15. The sintering temperatures may be 580~660° C. Through this optional step, the Ti—CaHAP can be more active in photocatalysis.

Figure 3:
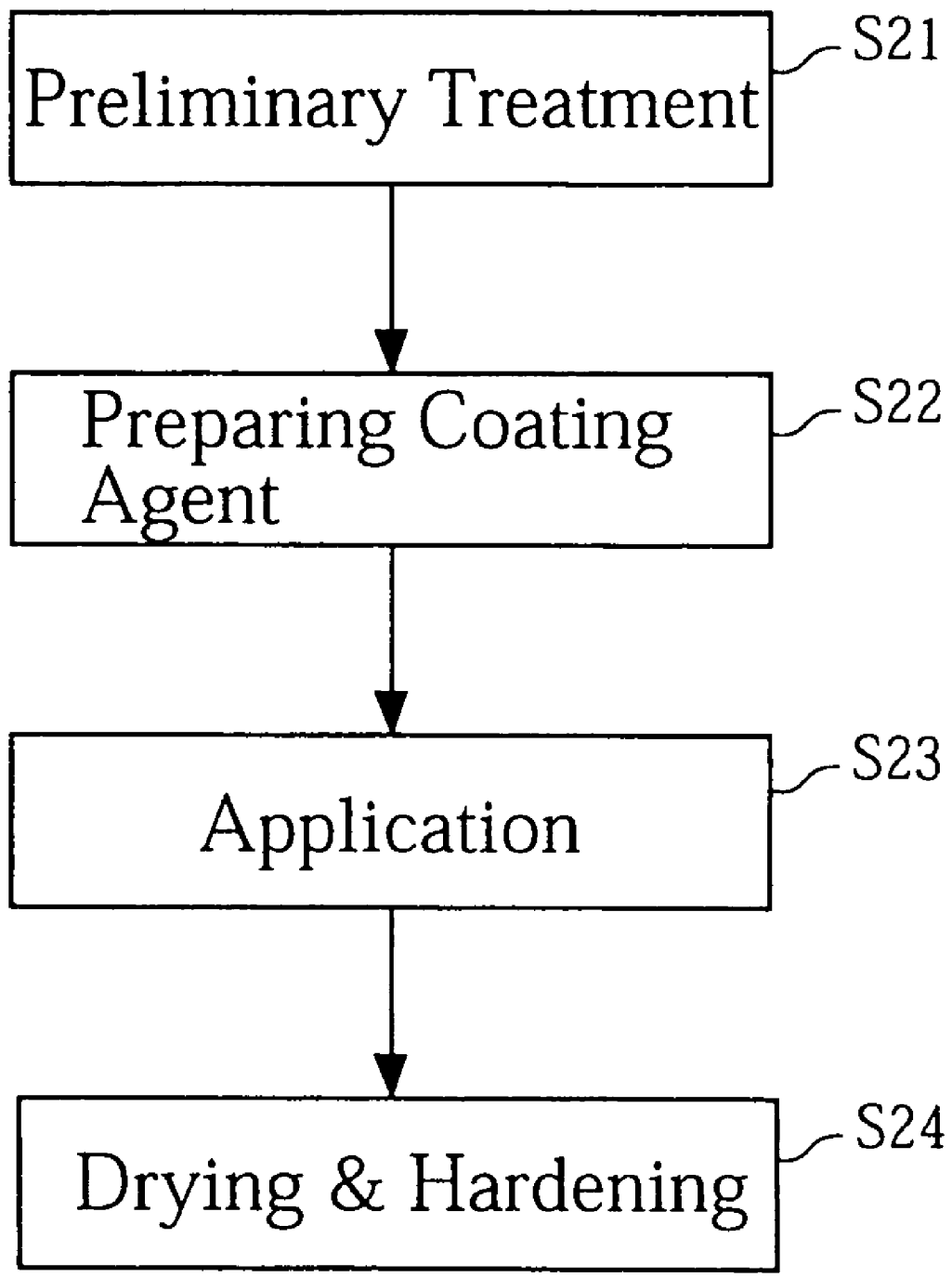
FIG. 3 shows how the antibacterial layer of the present invention is formed.

Referring to FIG. 3, the flow chart shows a fabrication procedure of an antibacterial layer containing the metal-modified apatite of the present invention. According to the chart, the powdered metal-modified apatite is first subjected to preliminary treatment at Step 21. The metal-modified apatite powder obtained in the above-described manner is composed of rather large particles (secondary particles) each of which in turn is composed of smaller particles (primary particles) cohering. The preliminary treatment at Step 21 is performed to break the cohering state of the particles.

Specifically, the preliminary treatment proceeds in the following manner. First, by addition of the metal-modified apatite to alcohol, an alcohol solution containing 1~15 wt % of metal-modified apatite is prepared. The alcohol used as a solvent may be isopropyl alcohol or ethanol, for example. Then, the alcohol solution is subjected to a milling process with the use of a ball mill for reducing the diameter of the secondary particles of the metal-modified apatite down to 5 µm or much smaller. The milling process may have several steps each utilizing zirconium balls of different diameters. For instance, a first milling step is performed for one hour with the use of balls having a diameter of 10 mm ("10 mm-balls"). Then, a second milling step for one hour with the use of 5 mm-balls, a third milling step for one hour with the use of 3 mm-balls, a fourth milling step for one hour with the use of 1.75 mm-balls, and a fifth or final milling step for one hour with the use of 1 mm-balls.

Instead of performing the above ball-milling, the alcohol solution may be filtered so that the obtained secondary particles of the metal-modified apatite will be no greater than 5 µm in diameter. Alternatively, the ball-milling and the filtering may both be performed. In this case, the secondary particles of the metal-modified apatite may be reduced in diameter to some extent by the ball-milling (at this stage the apatite particles are still greater than 5 µm in diameter) and then filtered to provide the desired finer secondary particles.

Then, at Step 22, an apatite-containing coating agent is prepared. Specifically, to produce the desired coating agent, the above-discussed alcohol solution (containing metal-modified apatite) is mixed into an inorganic base material such as heatless glass. (This base material should be inorganic so as not to be degraded by the metal-modified apatite.) According to the present invention, the resultant coating agent should contain 0.01-5 wt % of metal-modified apatite. Examples of heatless glass are ceraz (DAIWA INC.), JUVEL HGS (JUVEL ACE LTD.) and a room-temperature setting inorganic coating agent S00, which contains alkyl siloxane (NIHON YAMAMURA GLASS CO.,LTD.) as the main component.

Then, at Step 23, the prepared coating agent is applied to the prescribed portion(s) of an electronic device. The application may be effected by spraying, dipping into the coating agent, spin-coating, or roll coating.

Then, at Step 24, the applied coating agent is dried to form a hardened layer. When heatless glass is employed as inorganic base material to produce the coating agent, no extra heating treatment needs to be performed during the drying step, since the heatless glass hardens at room temperature.

The above layer formed on the electronic device contains 0.01-5 wt % of metal-modified apatite powder whose secondary particles are no greater than 5 µm in diameter. Advantageously, the thus composed antibacterial layer is substantially transparent and does not feel lumpy on the surface of the electronic device.

As described below, the inventors of the present invention produced several metal-modified apatite containing layers for comparison.

EXAMPLE 1

Formation of Metal-modified Apatite-containing Layer

Ti—CaHAP was prepared in a state of a powder (wherein the secondary particles had an average diameter of 5.7 µm, and the Ti ratio was 10 mol %). Then, the Ti—CaHAP was subjected to a preliminary treatment. Specifically, the Ti—CaHAP was added into isopropyl alcohol (IPA) to provide an alcohol solution containing a 5 wt % of Ti—CaHAP. Then, the alcohol solution was subjected to ball-milling including first to fifth processes. These five processes were each performed for one hour in common, but with the use of differently sized zirconium balls. The first process utilized zirconium balls having a diameter of 10 mm, the second process a diameter of 5 mm, the third process a diameter of 3 mm, the fourth process a diameter of 1.75 mm, and the fifth process a diameter of 1 mm. As a result of the multi-fold ball-milling, the average diameter of the secondary particles of the Ti—CaHAP was reduced to 3.5 µm, whereby the dispersibility of the Ti—CaHAP in the solution was improved. After the milling, the alcohol solution containing the broken-up Ti—CaHAP was subjected to filtering so as to remove Ti—CaHAP particles greater than 2.5 µm (in particle diameter) from the alcohol solution.

Then, the alcohol solution (0.2 gr.) was added to an inorganic base material (2 gr.) to provide the desired coating agent. The inorganic base material was a room-temperature setting type obtained by mixing S00 and UTE01 (both available from NIHON YAMAMURA GLASS CO.,LTD.) in the ratio of 10 to 1.

The thus produced coating agent was sprayed on a housing of an electronic device. Dried and hardened, the applied agent formed a Ti—CaHAP containing layer. This layer was highly transparent and not lumpy to damage the texture of the housing.

Evaluation of Photocatalysis

The photocatalytic function of the Ti—CaHAP containing layer was evaluated by a degradation analysis using methylene blue. Specifically, a prescribed portion of a glass plate (100×100 mm) was covered by a Ti—CaHAP containing layer formed by the application of the above-described coating agent. Then, the glass plate was immersed in an aqueous solution of methylene blue (10 μM) to be dyed. The dyed glass plate was exposed to the radiation of an ultraviolet lamp (10 mW/cm$^2$; 200-400 nm in wavelength) for 12 hours. As a result, the portion where the Ti—CaHAP containing layer was formed was discolored, while the remaining portion was not. This demonstrates that the applied ethylene blue was degraded by the action of the photocatalysis of the UV-irradiated layer.

Figure 4:
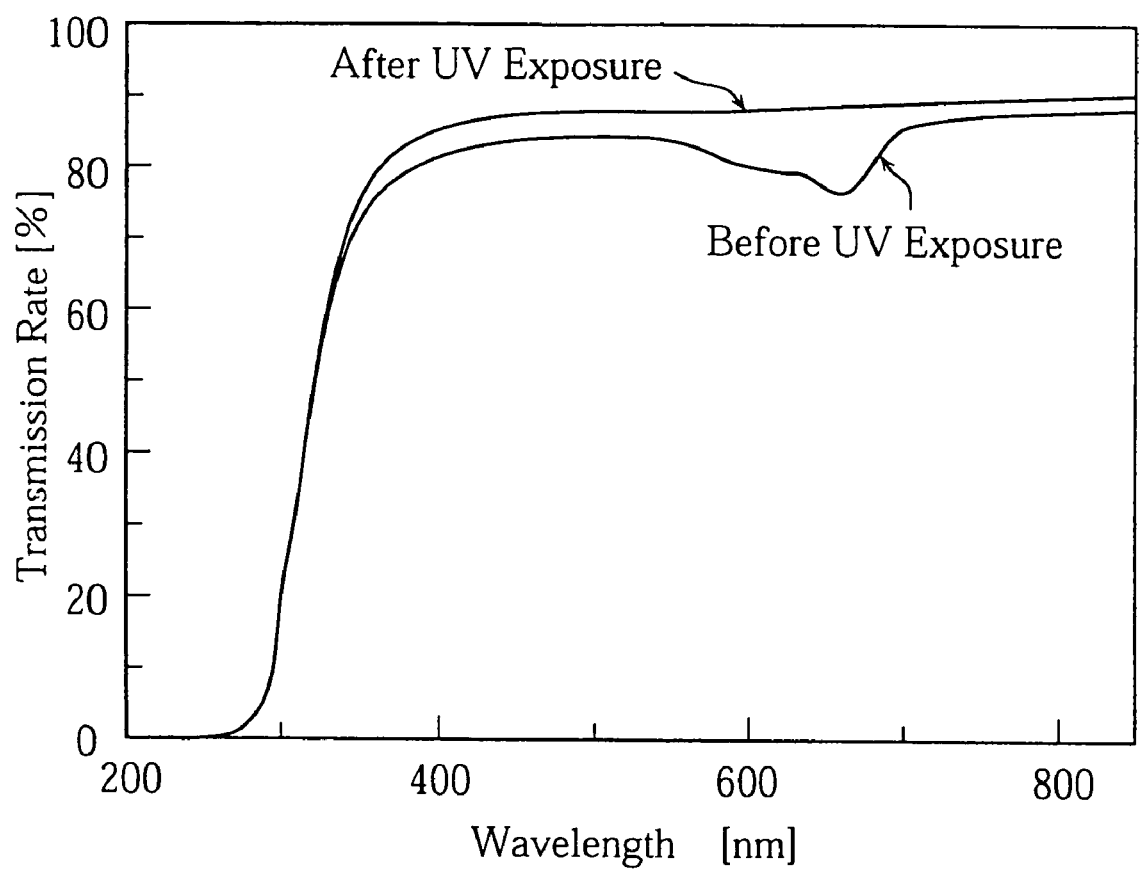
FIG. 4 is a graph illustrating how the relationship between the transmission rate of a glass plate and the wavelength of light is changed by ultraviolet irradiation to the antibacterial layer of the present invention.

FIG. 4 is a graph showing how the transmission rate of the ethylene blue-applied glass plate is changed by the irradiation of ultraviolet light. As seen from the graph, the transmission rate in a certain wavelength range is improved after ultraviolet light was irradiated. This result shows that the applied methylene blue was degraded by the photocatalysis of the Ti—CaHAP containing layer. Further, the graph of FIG. 4 shows that the glass plate, normally having a transmission rate of about 90% for visible light, has a transmission rate of about 85% in the presence of the Ti—CaHAP containing layer. In light of this, the Ti—CaHAP layer can be said to be highly transparent.

EXAMPLES 2 AND 3

A Ti—CaHAP containing layer was formed on the glass plate in the same manner as in Example 1 described above, except that the alcohol solution (added to an inorganic base material to produce the coating agent) contained 10 wt % (Example 2) or 15 wt % (Example 3) of Ti—CaHAP powder. Further, as in Example 1, the obtained layers were subjected to the measurement of the transmission rate. The results were that the transmission rates of Examples 2 and 3 were lower, partially or entirely in the visible light range, than that of Example 1.

EXAMPLES 4-6

A Ti—CaHAP containing layer was formed on the glass plate in the same manner as in Example 1 described above, except that the alcohol solution (obtained after the filtering process) contained secondary particles of Ti—CaHAP powder whose diameter was no greater than 8 μm (Example 4), 11 μm (Example 5) or 25 μm (Example 6). In Example 4, the outward appearance of the layer-coated housing was unacceptably spoiled by sporadic lumps of Ti—CaHAP particles. In Examples 5 and 6, a greater number of lumps of Ti—CaHAP particles were found than in Example 4, whereby the outward appearance of the housing was remarkably marred.

The present invention being thus described, it is obvious that the same may be varied in many ways. Such variations are not to be regarded as a departure from the spirit and scope of the present invention, and all such modifications as would be obvious to those skilled in the art are intended to be included within the scope of the following claims.

The invention claimed is:

1. An electronic device comprising:
   a target portion of antibacterial treatment; and
   a layer covering the target portion;
   wherein the layer contains an inorganic coating agent and 0.01~5 wt % of metal-modified apatite powder;
   wherein the metal-modified apatite is obtained by partially replacing Ca of calcium hydroxyapatite by Ti.

2. The electronic device according to claim 1, wherein a ratio of Ti to a total sum of Ca and Ti in the metal-modified apatite is 3~11 mol %.

3. The electronic device according to claim 1, wherein the metal-modified apatite comprises secondary particles each having a diameter of no greater than 5 μm.

4. An electronic device comprising:
   a target portion of antibacterial treatment; and
   a layer covering the target portion;
   wherein the layer contains an inorganic coating agent and 0.01~5 wt % of metal-modified apatite powder;
   wherein the inorganic coating agent comprises heatless glass.

* * * * *